United States Patent
Ren et al.

(10) Patent No.: US 8,427,152 B2
(45) Date of Patent: Apr. 23, 2013

(54) ELECTROMAGNETIC INTERFERENCE SUPPRESSION DEVICE AND MRI APPARATUS USING THE SAME

(75) Inventors: Zhongchang Ren, Shenzhen (CN); Liwei Yang, Shenzhen (CN); Tao Xu, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 277 days.

(21) Appl. No.: 13/051,862

(22) Filed: Mar. 18, 2011

(65) Prior Publication Data
US 2012/0089006 A1   Apr. 12, 2012

(30) Foreign Application Priority Data
Oct. 12, 2010   (CN) .......................... 2010 1 0504520

(51) Int. Cl.
*G01V 3/00*   (2006.01)

(52) U.S. Cl.
USPC ......................................................... 324/307

(58) Field of Classification Search .......... 324/300–322; 600/407–445
See application file for complete search history.

(56) References Cited

U.S. PATENT DOCUMENTS

| | | | | | |
|---|---|---|---|---|---|
| 5,560,360 | A | * | 10/1996 | Filler et al. ................... | 600/408 |
| 5,657,758 | A | * | 8/1997 | Posse et al. ................... | 600/413 |
| 5,706,813 | A | * | 1/1998 | Filler et al. ................... | 600/422 |
| 5,709,208 | A | * | 1/1998 | Posse et al. ................... | 600/410 |
| 5,879,299 | A | * | 3/1999 | Posse et al. ................... | 600/410 |

* cited by examiner

*Primary Examiner* — Brij Shrivastav
(74) *Attorney, Agent, or Firm* — Kory D. Christensen; Stoel Rivers LLP

(57) ABSTRACT

An electromagnetic interference suppression device and an MRI apparatus using such a device are disclosed. The MRI apparatus may include a main magnet, a gradient coil, an RF coil placed in a shielding chamber, a control system, and an electromagnetic interference suppression device.

15 Claims, 2 Drawing Sheets

ELECTROMAGNETIC INTERFERENCE SUPPRESSION DEVICE AND MRI APPARATUS USING THE SAME

CROSS-REFERENCE TO RELATED APPLICATION(S)

This application claims the benefit of Chinese Patent Application No. 201010504520.8, filed on Oct. 12, 2010, which is incorporated herein by reference.

TECHNICAL FIELD

The following disclosure relates to an electromagnetic interference suppression device and an MRI apparatus using such a device.

DETAILED DESCRIPTION

Figure 1:
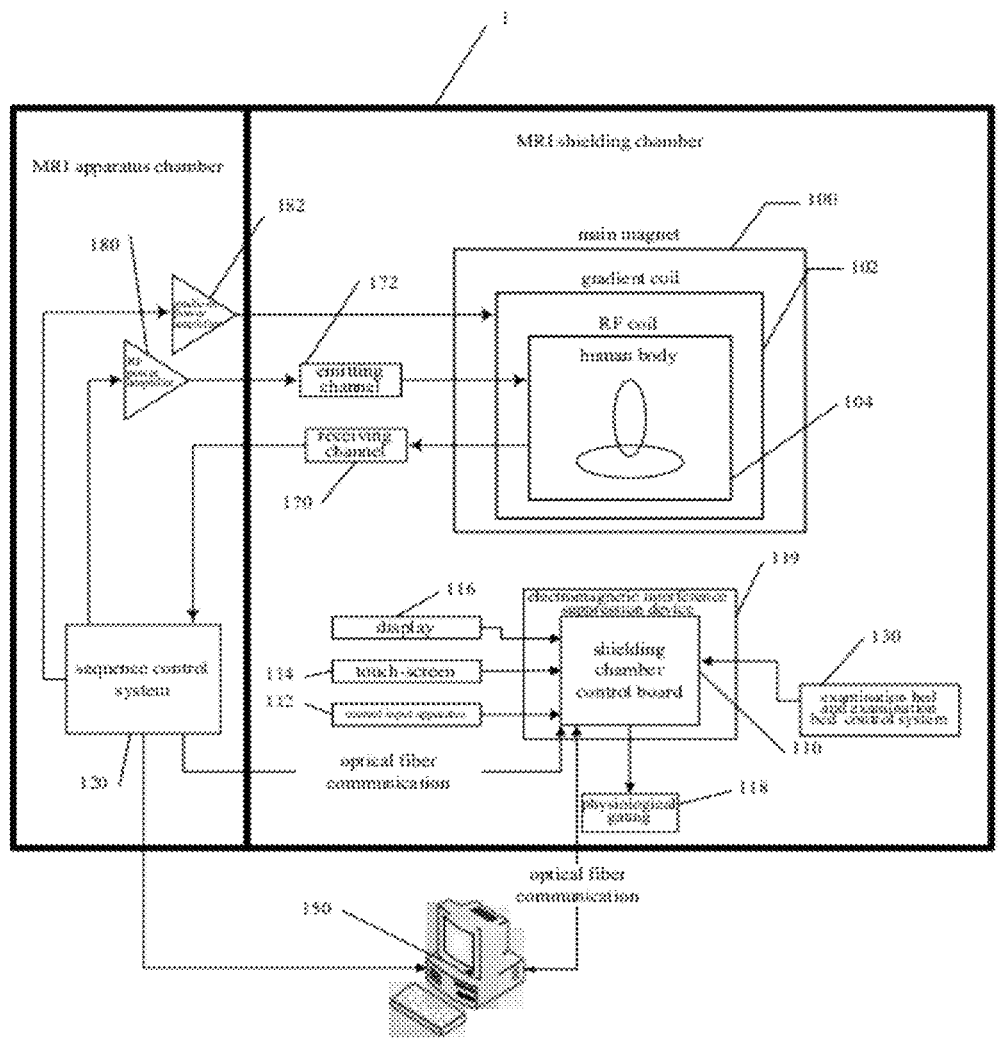
FIG. 1 is a block diagram of an MRI apparatus.

Magnetic Resonance Imaging (MRI) is one of the primary medical imaging technologies. It is one kind of tomography imaging, with high resolution for soft tissue, but without radioactive damage to human body. The basic principle of MRI is to obtain electromagnetic signals from the human body by utilizing the magnetic resonance phenomenon. A hydrogen proton has two energy levels under a static magnetic field, and when excited at radio-frequency (RF), the hydrogen proton will transit from the lower energy level to the higher energy level. If the RF pulse is removed, the hydrogen proton will then transit from the higher energy level back to the lower energy level, and emit RF energy. This RF energy will be received by the receiving coil of the MRI and processed to an MRI image.

A commonly used MRI apparatus may include a main magnet, a gradient coil, an RF coil, a gradient power amplifier, an RF power amplifier, a sequence control system, a console computer, and an interactive control system in a shielding chamber. The main magnet is used to provide a uniform basic magnetic field. The gradient coil is used to provide a magnetic field that varies with positions so as to distinguish different positions in space, and the RF coil is used to emit an exciting pulse and receive MRI signals. Since the signals received by the MRI RF coil are generally very weak, leaked electromagnetic waves from various electronic components in the system, such as the CPU, conversion circuit of the DC power source, etc., will result in serious interference to the image signals, and even cover the MRI signals.

As a result, the front end components, such as the main magnet, the gradient coil, and the RF coil, are generally disposed in a shielding chamber, whereas the main control components, such as the gradient power amplifier, the RF power amplifier, the sequence control system, and the console computer, are disposed in a control chamber or an apparatus chamber, which is isolated from the shielding chamber. The shielding chamber can only contain some control components with simple structure and low operating speed, which constitute an interactive control system. Thus, a complicated control cannot be implemented in the shielding chamber.

This results in a series of problems. For example, the main image operations can only be performed by the doctor outside the shielding chamber, and the doctor observes the patient through a transparent clapboard between the shielding chamber and the control chamber. Thus the doctor cannot communicate with the patient freely or change the positioning of the patient according to the situation. Even if the doctor works in the shielding chamber, he can only see some simple information displayed on a small dot matrix screen or section code screen in the shielding chamber, and if he wants to see the scan image, he has to go back to the control chamber, which makes the scanning process very inconvenient.

In one embodiment, an electromagnetic interference suppression device is provided in an MRI apparatus to allow complicated control in the shielding chamber. The electromagnetic interference suppression device may include a shielding box and a conducting plate, the shielding box including a plurality of shielding plates, the plurality of shielding plates enclosing a shielding space, the conducting plate being contained in the shielding space and fastened on the shielding plate of the shielding box, and the conducting plate being used to carry the interference source board that produces electromagnetic interference.

An MRI apparatus, according to one embodiment, may include a main magnet, a gradient coil, and an RF coil placed in the shielding chamber. A control system and an electromagnetic interference suppression device may be provided, in which the control system and the electromagnetic interference suppression device are disposed in the shielding chamber, the control system comprises a control board, the control board is fastened to and contained in the electromagnetic interference suppression device, the electromagnetic interference suppression device comprises a shielding box and a conducting plate, the shielding box includes a plurality of shielding plates, the plurality of shielding plates enclose a shielding space, the conducting plate is contained in the shielding space and fastened on the shielding plate of the shielding box, and the control board is fastened on the conducting plate.

In one embodiment, the electromagnetic interference suppression device and the MRI apparatus using the device containing the control board of the apparatus by the shielding box, wherein the control board produces electromagnetic interference to the MRI signals, thus electromagnetic interference is reduced; and the control board is fastened on the shielding box by means of the conducting plate, where the conducting plate forms a low impedance current loop, further reducing the electromagnetic interference of the control board to MRI signals. Therefore, an imaging control system, such as the shielding chamber control system described herein, can be disposed in the shielding chamber, such that the operator can implement a complicated imaging control in the shielding chamber, facilitating the operation of the MRI apparatus.

Referring to FIG. 1, there is shown a block diagram of a magnetic resonance imaging (MRI) apparatus according to one embodiment. The MRI apparatus 1 includes a main magnet 100, a gradient coil 102, an RF coil 104, a shielding chamber control system centering on a shielding chamber control board 110, a console system 150, a examination bed and examination bed control system 130, a sequence control system 120, an emitting channel 172, a receiving channel 170, an RF power amplifier 180, and a gradient power amplifier 182. The main magnet 100 provides a uniform basic magnetic field for imaging, and the gradient coil 102 provides a magnetic field that varies with positions so as to distinguish different positions in space. The RF coil 104 includes an emitting coil and a receiving coil. In one embodiment, the sequence control system 120 is used to output various control sequences required by the apparatus. The shielding chamber control system also includes a control input apparatus 112, a touch-screen 114, a display 116 and a physiological gating 118, which are connected with the shielding chamber control board. The console system 150 may include a personal computer or an industrial control computer.

In one embodiment, the main magnet 100, the gradient coil 102, the RF coil 104, the shielding chamber control system centering on the shielding chamber control board 110, the emitting channel 172, the receiving channel 170 and the examination bed and examination bed control system 130 are placed in an MRI shielding chamber, which is electromagnetically shielded from its surroundings. The sequence control system 120, the RF power amplifier 180, and the gradient power amplifier 182 are placed in the MRI apparatus chamber. In one embodiment, the console system 150 only needs to be placed in a normal control chamber.

The sequence control system 120 and the shielding chamber control board 110, the shielding chamber control board 110 and the console system 150 may be both connected with each other via a fiber communication link. The sequence control system 120 and the console system may be connected via a conventional data transmission connection.

During the period for signal emission, the sequence control system 120 outputs RF signals satisfying resonance conditions under the control of the console system 150 or the shielding chamber control system. The RF signals are power amplified by the RF power amplifier 180, and the amplified RF signals are emitted to the imaging target by the emitting coil in the RF coil 104 via the emitting channel 172, so as to excite the imaging target to produce nuclear magnetic resonance.

During signal acquisition, the receiving coil of the RF coil 104 senses and obtains MRI signals, then the MRI signals are received by the receiving channel 170 and the sequence control system 120, and are input to the console system 150 or the shielding chamber control board 110 after of the processes of pre-amplifying, frequency mixing, A/D conversion, and so on. Meanwhile, the sequence control system 120 sends out gradient control signals, which are power amplified by the gradient power amplifier 182 and output to the gradient coil 102, and the gradient coil 102 produces a gradient magnetic field for positioning the MRI signals in space. The MRI signals are processed by the console system 150 or the shielding chamber control board 110 to obtain an MRI image of the imaging target, and the MRI image is visually displayed to the operator by a display device or a display 116 in the console system 150. Meanwhile, the image information can be stored and retrieved as needed.

In one embodiment, the operator outside the shielding chamber can control and observe the MRI imaging by the console system 150. Meanwhile, the shielding chamber control system may similarly control the acquisition of the MRI signals and image processing by means of the shielding chamber control board 110, such that the operator in the shielding chamber may also control the imaging by means of the shielding chamber control system. The control input apparatus 112 equipped in the shielding chamber control board 110 may be a key-press, a tracking ball, a keyboard, and so on. The shielding chamber control system may also comprise a touch-screen 114, and by means of the touch-screen 114, control signals are input directly and MRI images are displayed. It may also introduce a large screen display 116, such as a liquid crystal display, for convenience of the operator to observe.

In additional to control imaging, the shielding chamber control board 110 may also connect with the examination bed and examination bed control system 130 to control the movement of the examination bed. Furthermore, by means of controlling the physiological gating 118, such as, cardiac electrical gating, cardiac electrical information may be enclosed into the MRI signals, so as to reduce motion artifacts, or else, the relaxation/contraction condition in various atria and ventricles may be observed by way of a movie. In this embodiment, the control board of the shielding chamber control board 110 is equipped with the disclosed electromagnetic interference suppression device 119, such that interference signals emitted by the electronic elements on the control board are shielded to ensure that there is no interference to the MRI signals.

In certain embodiments, it is only the shielding chamber control system that performs the process of information acquiring and processing, whereas the console system 150 controls the MRI imaging by means of communication with the shielding chamber control system. In other embodiments, it is only the console system 150 that can perform the process of acquiring and processing for MRI signals, whereas the shielding chamber control system transfers data and control signals by means of communication with the console system 150 to implement the controlling of the MRI imaging, or else, the shielding chamber control system only receives MRI images information transferred from the console system 150, so as to allow the doctor to observe images in the shielding chamber. In practice, the arrangement mentioned above varies as needed, and is not limited to the specifically disclosed approaches.

In one embodiment, the console system and the shielding chamber control system may communicate with each other through Ethernet under TCP/IP protocols, and the console system is connected with the shielding chamber control system via optical fiber communication. The console system and the shielding chamber control system both may control the acquisition of MRI signals and images processing. In other embodiments, a selector switch may be disposed for selecting whether the shielding chamber control system or the console system is to operate.

Figure 2:
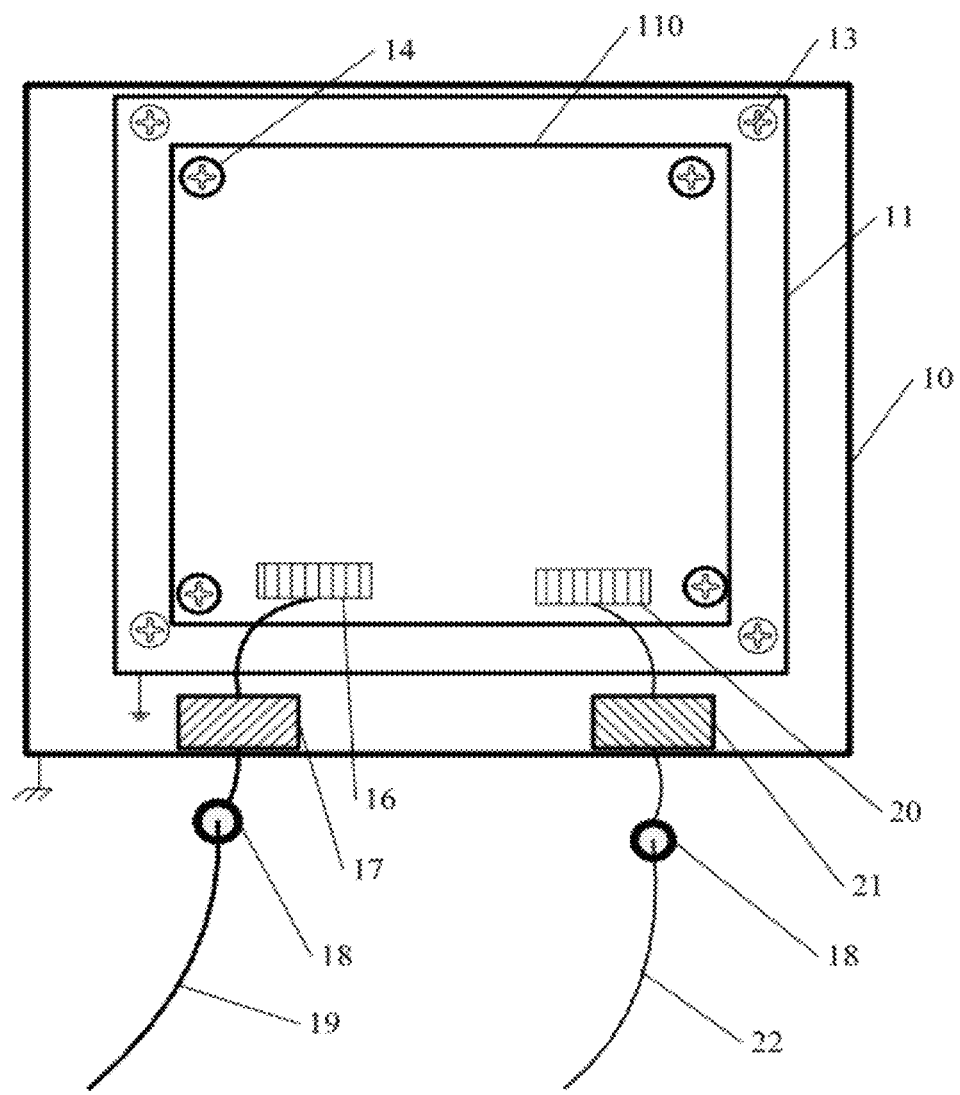
FIG. 2 is a schematic diagram of an electromagnetic interference suppression device.

FIG. 2 is a structural schematic diagram of an electromagnetic interference suppression device according to one embodiment. The control board 110 is an example of an interference source board. Likewise, as for the interference source board in other similar electronic devices, a similar electromagnetic interference suppression device may be designed. The control board 110 is a board with responsibility for control function in the shielding chamber control system, and the kernel of which is a central processing unit (CPU) or a field programmable gate array (FPGA), and it is equipped with a built-in storage or an external storage, logic devices, bus devices and various external devices and I/O. For example, the main control circuit board may be an industrial control board using an "x86" architecture, which may include the following components: CPU, north-bridge (driving the memory), memory, south-bridge (driving the PCI bus, providing multi-functional I/O), display control device, and so on. For example, the control board 110 may also be a control system with a kernel of the FPGA, and it may be embedded with a CPU soft core, wherein the FPGA may generate various external devices. When equipped with storage and a driving device, it forms a complete control system board.

As shown in FIG. 2, the control board 110 is fastened on the conducting plate 11 by bolts 14, and the conducting plate 11 is fastened on a shielding plate of the shielding box 10 by bolts 13. The conducting plate 11 and the shielding box 10 are both grounded. FIG. 2 does not depict the complete shape of the shielding box, but it should be appreciated by a skilled artisan that the shielding box is a close three-dimensional structure, which may be a cuboid, a cylinder, and so on. A suitable shape may be chosen according to actual requirements. In some embodiments, the shielding box 10 may comprise a plurality of shielding plates which are joined together, by bolts, screws, or push-pull structures, etc. In one embodiment, the shielding box is made of metal, such as copper, aluminum, aluminum alloy, etc. The conducting plate is made of materials with good electrical conductivity, such as metal, or alloy, and so on. The metal may be copper or aluminum. The grounding of the conducting plate may be achieved by connecting the metal plate via the bolt. Thus, the metal plate acts as a low impedance current loop, reducing the interference of the control board 110 per se to the surroundings. For further suppression, a plurality of conducting patches or conducting sponges can be applied to the electromagnetic interference suppression device. For example, the conducting patches or conducting sponges overlaps two adjacent shielding plates of the shielding box 10.

The control board 110 comprises the electronic components (such as processor, driver, interface) required for implementing the control of image scanning and displaying in the shielding chamber. In one embodiment, in order to further reduce the interference to the MRI signals caused by the control board 110, a signal filter 21 is introduced into the signal transmission line 22 by means of which the signal processing module 20 and other electronic devices (such as display 116) in the shielding chamber are connected, and a power supply filter 17 is introduced into the power transmission line 19 by means of which the power conversion module 16 and the external devices are connected. The type and parameters of the filters may be determined in accordance with the operation frequency range, magnitudes of voltage and current, the order of the interference carried, and impedance. Based on the embodiments above, a magnetic ring 18 may be arranged on the signal transmission line 22 and the power transmission line 19 so as to further suppress the interference. The magnetic ring 18 is mainly used to suppress the common mode interference. Furthermore, for the signal transmission line 22 and the power transmission line 19, the interference may be further absorbed by shielding, such that the electromagnetic interference is further suppressed.

The disclosed MRI apparatus suppresses most of the electromagnetic interference by means of placing the interference source board, i.e. the shielding chamber control board 110 in the electromagnetic interference suppression device 119, because the electromagnetic interference suppression device comprises a shielding box that contains the control board; and the conducting metal plate fastened at the bottom of the control board forms a low impedance loop, such that when the control board is working, its interference to the MRI signals is further reduced. Therefore, an imaging control system such as the shielding chamber control system described in the embodiments may be disposed in the shielding chamber, such that the operator may accomplish a complicated imaging control in the shielding chamber, facilitating the operation of the MRI apparatus.

In certain embodiments, the kernel control board of the display 116 in the shielding chamber may also be equipped with an electromagnetic interference shielding device similar to that in aforementioned embodiments; the whole MRI apparatus may only comprise a console system computer, and the console computer connects with two displays in the console and in the shielding chamber; in the MRI apparatus, there may be only a control system disposed in the shielding chamber, whereas the console system is omitted.

The above described embodiments should not be considered to limit the implementations of the disclosure to these descriptions. A skilled artisan can make simple modifications without departing from the concept of the disclosure, which will be deemed to be included in the protection scope of the disclosure.

What is claimed is:

1. A magnetic resonance imaging apparatus comprising:
a main magnet,
a gradient coil,
an RF coil placed in a shielding chamber,
a control system, and
an electromagnetic interference suppression device,
wherein the control system and the electromagnetic interference suppression device are disposed in the shielding chamber, the control system comprises a control board, the control board is fastened on and contained in the electromagnetic interference suppression device, the electromagnetic interference suppression device comprises a shielding box and a conducting plate, the shielding box comprises a plurality of shielding plates, the plurality of shielding plates enclose a shielding space, the conducting plate is contained in the shielding space and fastened on the shielding plate of the shielding box, and the control board is fastened on the conducting plate.

2. The magnetic resonance imaging apparatus according to claim 1, wherein the shielding box further comprises a plurality of conducting patches or conducting sponges, the conducting patches or conducting sponges overlapping two adjacent shielding plates.

3. The magnetic resonance imaging apparatus according to claim 1, wherein the conducting plate and the shielding box are made of metal.

4. The magnetic resonance imaging apparatus according to claim 1, wherein the control board is fastened on the conducting plate via bolts.

5. The magnetic resonance imaging apparatus according to claim 4, wherein the conducting plate is fastened on a shielding plate via bolts.

6. The magnetic resonance imaging apparatus according to claim 1, wherein the control system further comprises a liquid crystal display, which is connected with the control board.

7. The magnetic resonance imaging apparatus according to claim 1, wherein the control system further comprises a touch-screen, which is connected with the control board.

8. The magnetic resonance imaging apparatus according to claim 1, wherein, further comprising a second control system disposed outside the shielding chamber, wherein the second control system is connected with the control system in the shielding chamber by optical fiber communication.

9. An electromagnetic interference suppression device, comprising:
a shielding box and a conducting plate, wherein
the shielding box comprises a plurality of shielding plates,
the plurality of shielding plates enclose a shielding space,
the conducting plate is contained in the shielding space and fastened on the shielding plate of the shielding box, and
the conducting plate is used to carry an interference source board that produces electromagnetic interference.

10. The electromagnetic interference suppression device according to claim 9, wherein the conducting plate is a metal plate.

11. The electromagnetic interference suppression device according to claim 9, wherein, the conducting plate is fastened on the shielding box via metal bolts.

12. The electromagnetic interference suppression device according to claim 9, wherein the shielding box further comprises a plurality of conducting patches or conducting sponges, the conducting patches or conducting sponges overlapping two adjacent shielding plates.

13. The electromagnetic interference suppression device according to claim 9, wherein the interference source board is fastened to the conducting plate via metal bolts.

14. The electromagnetic interference suppression device according to claim 9, wherein the interference source board communicates signals and energy with electronic devices outside the shielding box via leads, the signal line being encircled by a magnetic ring to suppress common mode interference.

15. The electromagnetic interference suppression device according to claim 14, wherein the lead is a shielded lead.

* * * * *